United States Patent [19]

Behrend

[11] 4,020,522

[45] May 3, 1977

[54] BRISTLE RING FOR USE IN DENTAL CARE

[76] Inventor: Hans Behrend, Osloer Strasse 99.1, Berlin 65, Germany

[22] Filed: Dec. 18, 1975

[21] Appl. No.: 641,920

[30] Foreign Application Priority Data

Dec. 21, 1974 Germany .......................... 2461055

[52] U.S. Cl. .................................... 15/180; 15/28; 32/59
[51] Int. Cl.² ........................................... A46B 7/08
[58] Field of Search ............... 15/179, 180, 28, 29; 32/58, 59; 128/56

[56] References Cited

UNITED STATES PATENTS

| 1,391,221 | 9/1921 | Tuttle | 15/198 UX |
| 1,526,579 | 2/1925 | Albertson | 15/198 |
| 3,177,510 | 4/1965 | Mack | 15/29 |
| 3,335,444 | 8/1967 | Weiler | 15/179 |

FOREIGN PATENTS OR APPLICATIONS 456,531 7/1968 Switzerland .......................... 15/28

Primary Examiner—Peter Feldman
Attorney, Agent, or Firm—Michael J. Striker

[57] ABSTRACT

A bristle ring for use in dental care comprises a rotating cup, at least two rows of bristles arranged in ring shape, the bristles being mounted in said cup and forming a configuration of outwardly diminishing cross-section of frusto-conical shape, the foremost portions of the bristles having a frusto-conical shape of outwardly diminishing cross-section and the inner row of bristles extending beyond the adjoining outer row so as to protrude beyond said frusto-conical configuration and form an outer circular sharp edge.

9 Claims, 6 Drawing Figures

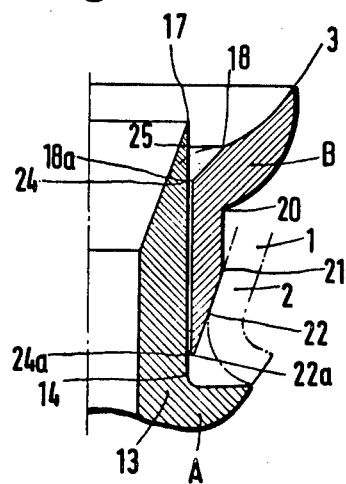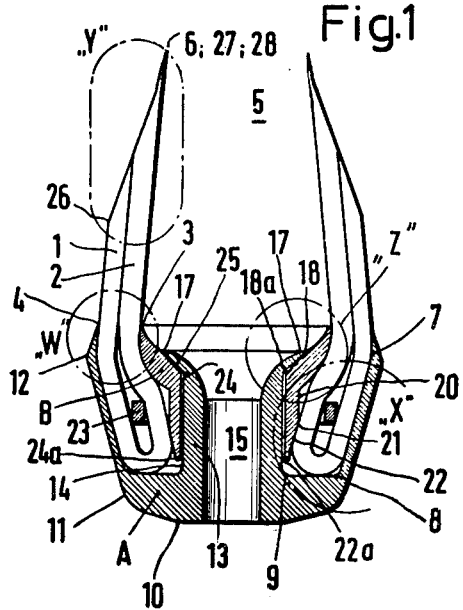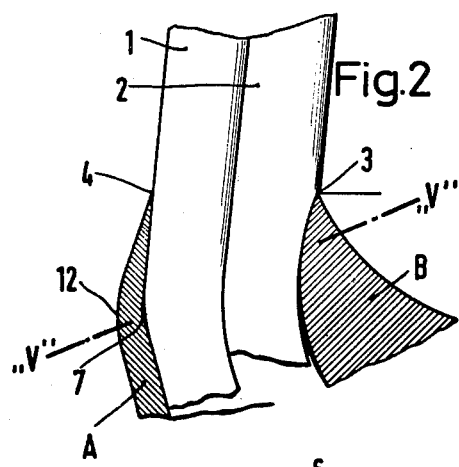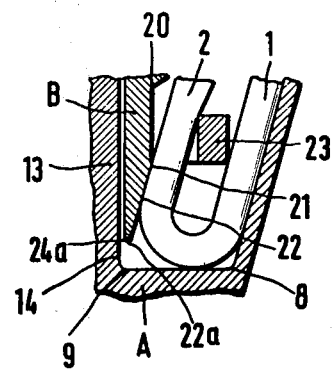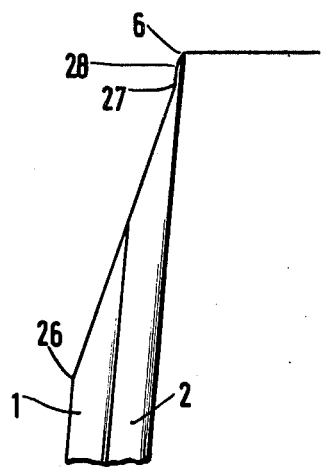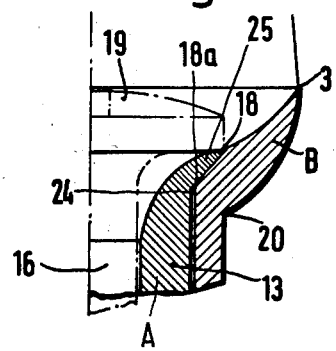

BRISTLE RING FOR USE IN DENTAL CARE

The conventional tooth cleaning care by means of toothbrushes and antiseptic products of various types has not accomplished to maintain the teeth in good health to the desired degree.

The designation "tooth cleaning" does not do justice to the facts since it does not include a health preserving agent which would prevent caries formation and paradontopathoses even though the tooth cleaning would be carried out several times per day. The known toothpastes consist of a toothpaste base, the so-called dentifrice, and the effective agents incorporated therein. However, these are not pharmaceutical products which cause the organism of the caries to disappear or the paradontopathoses to heal, but they contribute only to the reduction of these general dental diseases in connection with the conventional tooth-cleaning care by means of toothbrushes. This is too little to maintain human teeth in good health and to forestall diseases of the tooth socket and loosening of the teeth.

Neither is it possible on the basis of the present state of research to effectively attack the causitive agents of decay by gargling or mouth rinsing by means of mouthwash since the medical mouthwash has only a limited disinfecting action and merely leaves the user because of the antiseptic aftertaste with a refreshing feeling in the mouth and pharynx.

Bristle bodies have become known in which the bristles are arranged in bundles and the bristle points are rounded, pointed or arranged in V-shape and which therefore partly penetrate into the interstices of the teeth or massage the gum thoroughly and in a delicate manner. However, these treatments likewise cannot remove the causitive agents of tooth caries and of tooth socket diseases.

The modern mouth hygiene in which a pulsating water jet or an anticaries chewing gum or a fluorinated anitcaries drinking water is used can likewise not prevent caries formation, paradontosis and other tooth socket diseases and certainly cannot reverse them and cannot avoid mouth odor.

Another method of tooth care consists in sweeping over the teeth with the brush in the direction of the gum towards the crown of the teeth, while simultaneously subjecting the mucuous membrane to a massage, for instance by means of the impressively constructed and electrically driven toothbrushes.

More recent proposals while including manufacturing improvements of the mechanical-motor drives have not changed the above principles. It can therefore be said in summary that the electrical toothbrush has the same wellknown shortcomings as the normal tooth-cleaning care and in case of the lower quality types, does not even reach the same level.

In the course of the years and with the knowledge of the well-known problems, rotating bristle cups have become known, for instance in U.S. Pat. No. 3,177,510 or in case of Weiler, U.S. Pat. No. 3,335,444 with their "miniature brush or combination brush" which, however, does not constitute an advance in preventing the diseases.

The present invention enables in a simple manner to prevent and cure the so-called tooth and mouth diseases by employing a bristle ring in form of a frustum of a cone. This bristle ring is specifically characterized by the fact that the innermost bristle layer which accordingly has the thickness of a single bristle protrudes beyond the next bristle layer. There is therefore at the tip of the frustum of the cone an annular bristle ring cutting edge of the thickness of a singel bristle. This makes it possible to move antiseptic compounds to the place which usually cannot be reached by the conventional toothbrushes or other dental care media, that is the gingival edge or furrow.

The invention proceeds from the basic finding that the diseases have a common origin, to wit the deposit of decay causing materials in the gingival edge. The invention furthermore proceeds from the finding that the carbohydrates which in connection with specific microorganisms and the fission fungi are responsible for the caries and paradontopathoses could heretofore exert their destructive action without interference in the mouth. The invention accordingly, by removing the food residues and thus the carbohydrates and also bacteria and fungi from the destructive area of the gingival edge, accomplishes a prophylactic and curative action.

The inventor takes into consideration the fact that the decay of the hard dental substance is not caused by a bacillus but by the chemical-parasitic activities at the gingival edge caused by food residues which cannot be removed by conventional teeth cleaning. It stands to reason accordingly that dental diseases which are diagnosed as nutritive transgressions cannot be cured by means of dietary rules such as avoiding of hard candies, chocolate, white bread or cake.

According to a further invention, the inner face of the bristle ring is in the form of a frustum of a cone that has an upwardly reduced diameter. This frusto-conical inner space of the bristle ring is filled with an infection preventing agent, an antisepticum, which, upon rotation, assures a refreshening disinfecting neutralizing rinse and which at the same time causes a mild rinsing around the hard dental substance.

Further features of the invention and advantages will appeaar specifically from the following description in which reference will be made to the attached drawings. These drawings illustrate the following:

FIG. 1 is an enlarge overall view in form of an axial section through a gingival edge goblet or cup with the functionally important bristle and goblet-shape according to the invention;

FIG. 2 is an enlargement in section of FIG. 1 showing the annular cutting edges 3 and 4 which narrowly embrace the protruding bristles 1 and 2 and push them in the direction "V—V" and thus shape them as desired;

FIG. 3 is a sectional enlargement "X" of FIG. 1 showing the inner end of the inner cup B with the frustum of the cone 22 which leads to an annular cutting edge 22a which supports the bristle layers 1, 2 in the area of the bottom 8, 9 of the inner wall of the outer cup in their uniform distribution and causes the filled-in ring 23 to slide into an unrestrained higher position and thus permits or enables a slim outer shape of the cup A;

FIG. 4 is a sectional enlargement "Y" of FIG. 1 showing the tips of the two bristle layers 1, 2 with the functionally important edge of the innermost bristles: bristle ring 27, 28, bristle ring cutting edge 6;

FIG. 5 is a sectional enlargement "Z" of FIG. 1 illustrating the cutting edge 3 in the upper portion of the inner cup B formed by merging of the convex arcs 20, 3 and the spherical depression 18, 3 of which the lower area is shaped as a cone depression 18, 18a so as to receive the annular cutting edge shaped end piece 17a of the flange of the rivet stub 25 of the outer cup A, thus to provide for a smooth transition to the spherical depression 18, 3 and furthermore to provide for a firm connection and central disposition of the two part cup-shaped receiving body;

FIG. 5a shows the sectional enlargement "Z" of FIG. 1 as illustrated in FIG. 4 and supplemented in order to explain the entire centering arrangement in the condition prior to the formation of the flange. The inner cup B sits with its cylindrical part 24, 24a on the center axle 13 of which the cylindrical outer surface 14, 17 constitutes the counterface to a narrow seating. After mounting the brush layers 1, 2 by means of a known ring 23 and of the inner cup V the rivet stub 25 of the center axle 13 of the outer cup A is provided by means of a riveting stamp with a flange around the edge 18a of the inner cup B in a manner that the center axle cutting edge 17a meets the edge 18 of the inner cup 4 and thus forms a permanent transition.

FIG. 1 shows a dental gingival edge cup which is formed of a non-noble material with a galvanically applied coating or of a noncorrosive steel. The brushes which are arranged in two layers, 1, 2 are lined up and locked in in the annular notch 3, 4 which is formed by the annular cutting edge-shape diameter 3 in the upper end of the inner cup B and by a special conical annular cutting edge 4 in the upper end of the outer cup A. The bristle layers 1, 2 are thus formed around a frusto-conical space 5 which serves to receive water or an antisepticum. The bristle tips 6 and bristle ring 27, 28 penetrate as shown in FIG. 4 which illustrates the segmental enlargement Y of FIG. 1, into subgingival furrow between enamel and epithelium and, according to the invention, cause, in conjunction with the antisepticum, a disinfecting and neutralizing action regarding the chemical-parasitic developments.

The outer cup A is formed as follows: The inner face of the outer wall leads from the upper conical ring cutting edge 4 as shown in FIG. 2, of the bristle exit opening towards the inner bottom surface 8, 9, at the beginning getting wider (4, 7) and then inwardly conical (7, 8). The outer wall on the other hand at its outer face consists of the lower base surface 10, the transition radius 10, 11 and, towards the upper end and parallel to the inner wall, of the jacket of the cone 11, 12 which connects in its upper part with an inwardly reduced diameter conical turn 12, 4. The outer cup A with its outer periphery, the rounded transition 12 between the outer cones and the transition radius 10, 11 does not furnish any approach to that part of the tooth which extends freely into the mouth. By means of the cooperation according to the invention of the inner cup B, outer cup A, with the outer conical part 11, 12 (jacket of the frustum of the cone) and bristle layers 1, 2, it is possible to attain the triangular relation from height to diameter of the finished cup as shown in FIG. 1 and thus forms the slim shape which solely permits the gingival edge care. The outer cup A which consists of a single piece is provided in its inner space with a centrically disposed centering stub 13 of which the outer face as shown in FIG. 5a constitutes a centering surface 14, 17 on which the inner cup B with a narrower fit is fixed through its cylindrical bore 24, 24a. The centering stub 13 is centrically and axially provided with a bore 15 of which the clearance is taken up by a screw 16 with a tight fit and which thus assures a smooth centric rotation. The upper end of the centering stub 13 is the rivet stub 25 with the rotating centering stub 17 as shown in FIG. 5a. This cutting edge impacts after forming the flange onto the edge 18 of the inner cup B. The depression is dimensioned so that during mounting the screw head 19 is completely accommodated.

The upper edge of the inner cup 12 as shown in FIG. 5 (segmental enlargement Z of FIG. 1) is provided as an annular cutting edge 3 as shown further in FIG. 2. Thus, all metal contact with the hard dental substance during rotation of the bristle layer 2 for rinsing of the tooth crown surfaces in the frusto-conical space 5 is effectively prevented. The outer circumference of the inner cup 4 is formed as follows: starting from its upper annular cutting edge shaped diameter 3 via a convex radius 3, 20 and a connecting cylindrical part 20, 21 it merges into a frustum of a cone 22 towards an annular cutting edge 22a. The frustum of the cone 22 in the lower portion of the inner cup B assists the ring 23 as shown in the segmental enlargement X of FIG. 1 (see FIG. 3) to an easy alignment within the bristle layers 1, 2 and it makes possible together with the upper convex arc 3, 20 to obtain the mouth adapted medically required shape of the outer cup A, that is the slim shape which is indispensable for use in the mouth. The inner contour of the inner cup B is composed of the spherical depression 3, 18 which starts at the upper annular cutting edge 3 and is further composed of an adjoining depression of the cone 18, 18a and a cylindrical portion 24, 24a parallel to the outer cylinder 20, 21 up to the lower annular cutting edge 22a. The depth of the spherical depression 3, 18 is figured so that the cutting edge 17 of the central stub at the rivet part 25 and the head 18 of the screw 16 of the mandrel is completely received and thus cannot have an abrasive and thus damaging effect for the enamel of the crown of the tooth.

The inner shape of the outer cup A together with the outer shape of the inner cup B has the effect that the coaxially arranged two-bristle layers 1, 2 dispose between the two cups by means of a ring 23 as shown in U.S. Pat. No. 3,335,444 and in FIG. 3 (segmental enlargement X of FIG. 1). This coaxial form of the two bristle layers is made in a way that the protruding bristles in their inner form 3, 6 exhibit a cone which has a slightly diminishing cross-section upwards while the outer shape 4, 6 consists of two jackets of a frustum of a cone in a manner that the protruding part 4, 26 is slightly inwardly inclined and the upper adjoining part 26, 27 beginning after the first half of the free length has a shape which is inwardly of cone-shape and forms as end part a bristle ring 27, 26, 6 of the thickness of the bristles used. The separate bristle ring 27, 28, 26 extends beyond the cone section 26, 27. This bristle ring is pointed at its tip throughout the entire cross-sectional width. Thus a bristle ring cutting edge is formed as shown in FIG. 4 (segmental enlargement Y of FIG. 1).

For making use of the invention for gingival edge care the bristle tip 6 is first rinsed with boiling water. The rows of teeth are then moved to bite position. The rotating bristle cutting edge 6 is then adjusted into the gum pocket and at the upper and lower bite is passed back and forth two or three times vestibularly, labially and buccally while in case of oral palatal lingual gingival edge care, the rows of two teeth are opened and the entire procedure is then repeated. The rotating functionally important bristle tip just penetrates cautiously into the gingival edge or furrow.

The invention permits to preserve the natural enamel transition, the enamel edge and the cementum coating of the root. The ligamentum circulare, the subgingival epithelium texture, the marginal gingiva, the interdental papillae and the cervical edge is freed of the close adherence by fermenting food residues and the recurring deposit of tartar is avoided.

A further advantage of the invention resides in the fact that the bristle ring (gingival edge cup) is adapted to the anatomical dimensions of the mouth, the rows of teeth and the gingival edge in their cross sections, angular and curvature characteristics. Thus, during the gingival edge care and the rinsing around the surfaces of the teeth, no particular safety measures are necessary as against the rotating parts. Experience has taught that the organisms again and again try to penetrate into the gingival edge during biting, chewing and grinding efforts or that they settle on the approximal surface of adjoining lateral tooth faces. To prevent all this daily gingival edge care should be carried out.

The new bristle ring (gingival edge cup) is centrally and axially received by means of a so-called mandrel, that is a plug which is provided with a disc and a thread with which the main screw cooperates. The ring is thus fixed in a handle or angle piece with an integral drive mechanism.

The bristle ring of the invention (gingival edge cup) while carefully rotating with its specific bristle edge penetrates into the subgingival furrow between enamel and epithelium which cannot be reached by a toothbrush. This is the notch which is bordered by the ligamentum circulare. The ring thus grasps the organisms which cause caries and paradontopathoses detaching these agents and thus permiting them to be rinsed away.

The gingival edge care according to the invention and the thus accomplished hygiene effect results in a removal of the carbohydrates which are present as food residues in the destruction area of the gingival edge. Thus, the nutritive medium for the specific microorganism, bacteria and fungi is withdrawn which otherwise would act as catalyst for the fermentation and the acid formation and thus would be responsible for the destruction of the hard dental substance (caries) and the tooth bed diseases (paradontopathoses.)

Careful observations have shown that the entrance to the gingival furrow between enamel and epithelium is not only accessible to the dentist, but also to the layman which makes use of the bristles of the invention. The invention thus constitutes a bristle ring which on one hand grasps the accumulated food residues in their hiding place of the subgingival furrow between enamel and epithelium and removes them but also accomplishes a total disinfectant rinsing of the tooth faces. The invention shows the stage accomplished by the specific bristle cut which, through its uniform rotation, rinses the tooth faces by means of the water or antisepticum disposed in the enclosed space of the frustum of the cone. Thus, because of the compulsive rotating and whirling effect it is accomplished that the almost continuously adhering fine deposits, particularly at the labial and buccal surfaces of the necks of the teeth which reach even into the depth of the gingival furrow are lifted and the hard composition of the tooth appears in their original transparency.

With the present invention the specific bristle points with the set number of rotations and force of rotation reach the three breeding places of the damaging germs and by adding an antisepticum the germs are killed and cannot enter the body of the patient. With this type of gingival edge care, no side effects are observed and there is no danger of reactions due to hypersensitivity (allergies).

The bristle ring (gingival edge) because of its large wetting ability within the tip of the bristles, causes the antiseptic agents to accumulate in the subgingival furrow and reach into the smallest spaces between the texture. The specific bristle tips of the invention lift the microscopically thin bacterial deposit from the tooth enamel and out of the slots of the subgingival furrow.

By means of the invention not only is there avoided the formation of a film of food adhering to the transparency of the enamel-cementum coating at the vital teeth within the mouth, but also the oxides which form at permanent tooth replacement, such as metal crowns, pivot teeth, parts of bridge replacements, etc, are removed.

A further advantage of the invention is that the rinsing effect on the enamel edge, the enamel and cementum coating which cover the teeth restore the natural transparency and permit the true colors of the dental bone to shine through and thus to become visible while a "brilliant white" of the tooth crown cannot be accomplished by means of toothpaste or powder.

Through the invention of the gingival edge cups everybody can help cause the general disease, paradontosis, to heal and to cause a reduction of the acid formation in the gingival edge and eventually to stop it completely so that caries could not occur either.

The gingival edge cup is intended for the dental practice to obtain healing of paradontopathoses. These are diminished already after a few treatments. The requirement therefor is that the tartar deposits which are more or less hard and which are deposited on the neck of the tooth and in the subgingival space are removed thoroughly.

I claim:
1. A bristle ring for use in dental care comprising a plurality of bristles arranged in ring shape in a depth of at least two rows of bristles, a rotating cup, the bristles being mounted with their base in said rotating cup and, starting from their mounting in said cup, being slanted conically inwardly in an upwards diminishing cross-section, and the forward portions of the outer bristles of said ring having a frusto-conical shape of upwardly diminishing section and the innermost bristle extending beyond the outwardly adjoining row of bristles so as to protrude beyond said frusto-conical shape and to form an outer circular sharp edge (6).

2. The bristle ring of claim 1 wherein the inner face of said bristle ring forms a central frusto-conical space (5), the said space being adapted to receive and hold an antiseptic composition.

3. The bristle ring of claim 1 wherein the two conically slanted rows of bristles constitute two conjoint frusto-conical jacket surfaces.

4. The bristle ring of claim 1 which includes retaining members in form of an outer ring (A) and an inner ring (B), the outer ring (A) having generally a U-shaped and embracing the inner ring (B) in a manner that the inner ring and the bristle rows (1, 2) are wedged between the two shanks of the U.

5. The bristle ring of claim 4 wherein the end of the outer shank of the outer ring (A) is formed as a cone (4, 12) which has a diminishing cross section in the direction of the outer ends of the bristles while the shank of the U in the opposite direction (11, 12) likewise has a diminishing cross section towards the base (10) of the U.

6. The bristle ring of claim 4 wherein the inner shank of the U of the outer ring (A) is formed as a centering plug (13) and wherein a rivet stub (25) is provided which constitutes a connection between the outer ring (A) and the inner ring (B).

7. The bristle ring of claim 6, wherein the inner ring (B) of the cup is formed in profile as a straight angle of which one leg with its inner face has contact with the inner row of bristles (2) and with its outer face has contact with said rivet stub (25), and which bristle ring includes a screw (16, 19) and a centering plug (13), the screw leading through the centering plug and being seated on the rivet stub.

8. The bristle ring of claim 1 wherein said rotating cup holding the bristle layers (1, 2) is formed of a thermoplastic material.

9. The bristle ring of claim 1 which includes an inner and outer cup for holding said bristles, the bristles being fastened to said cups by means of an adhesive.

* * * * *